US00PP27149P2

(12) United States Plant Patent
Hughes

(10) Patent No.: US PP27,149 P2
(45) Date of Patent: Sep. 13, 2016

(54) ***BEGONIA* PLANT NAMED 'CANARY WING'**

(50) Latin Name: ***Begonia* hybrid**
Varietal Denomination: Canary Wing

(71) Applicant: Jared Edward Hughes, Cardington, OH (US)

(72) Inventor: Jared Edward Hughes, Cardington, OH (US)

(73) Assignee: Groovy Plants Ranch LLC, Cardington, OH (US)

( * ) Notice: Subject to any disclaimer, the term of this patent is extended or adjusted under 35 U.S.C. 154(b) by 34 days.

(21) Appl. No.: 14/544,980

(22) Filed: Mar. 11, 2015

(51) Int. Cl.
*A01H 5/02* (2006.01)

(52) U.S. Cl.
USPC ..... Plt./343

(58) Field of Classification Search
USPC ..... Plt./343
CPC ..... A01H 5/0238
See application file for complete search history.

*Primary Examiner* — Kent L Bell
(74) *Attorney, Agent, or Firm* — Penny J. Aguirre

(57) ABSTRACT

A new cultivar of *Begonia* of hybrid origin named 'Canary Wing', that is characterized by its trailing plant habit, its pendant flowers that are reddish pink in color, and its foliage that emerges golden chartreuse in color maturing to a chartreuse green color.

2 Drawing Sheets

Botanical classification: *Begonia* hybrid.
Cultivar designation: 'Canary Wing'.

BACKGROUND OF THE INVENTION

The present invention relates to a new and distinct cultivar of *Begonia* plant of hybrid origin, botanically known as *Begonia* 'Canary Wing' and will be referred to hereafter by its cultivar name, 'Canary Wing'.

The Inventor discovered the new cultivar in May of 2014 as a naturally occurring branch mutation of a plant grown from seed of the *Begonia* seed strain Dragon Wing® Pink (no cultivar name available and not patented) in a container block at his nursery in Delaware, Ohio. The Inventor initially isolated a branch on 'Dragon Wing Pink' with gold variegated leaves and made subsequent cuttings selections to develop and select 'Canary Wing' with solid gold foliage.

Asexual propagation of the new cultivar was first accomplished by the Inventor by stem cuttings in Cardington, Ohio in May of 2014. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar, which in combination distinguish 'Canary Wing' as a new and distinct cultivar of *Begonia*.

1. 'Canary Wing' exhibits a pendulous to trailing plant habit.
2. 'Canary Wing' exhibits pendant flowers that are reddish pink in color.
3. 'Canary Wing' exhibits foliage that emerges golden chartreuse in color maturing to a chartreuse green color.

The parent of 'Canary Wing' differs from 'Canary Wing' in having young and mature foliage that is dark green in color and in having a more upright plant habit. 'Canary Wing' can be most closely compared to the *Begonia* cultivars (no cultivar names available) of the seed strain Dragon Wing® Red (not patented) and 'Dragon Wing® White' (not patented). Both cultivars are similar to 'Canary Wing' in leaf size and overall growth habit. Dragon Wing® Red differs from 'Canary Wing' in having foliage that is darker green in color, in having flowers that are red in color, and in having a more upright plant habit. Dragon Wing® White differs from 'Canary Wing' in having foliage that is darker green in color, in having flowers that are white in color, and in having a more upright plant habit.

BRIEF DESCRIPTION OF THE DRAWINGS

The accompanying colored photographs illustrate the overall appearance and distinct characteristics of the new *Begonia*. The photographs were taken of plants 1 month in age as grown in 4-inch containers in a greenhouse in Cardington, Ohio.

The photograph in FIG. 1 provides a view of numerous plants of 'Canary Wing'.

Figure 1:
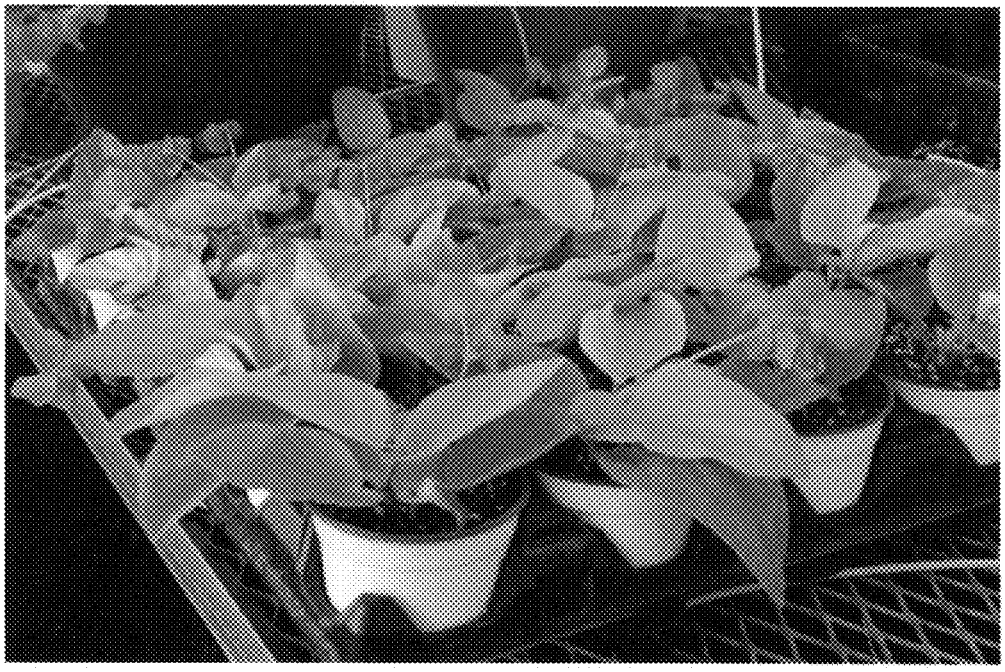
Figure 2:
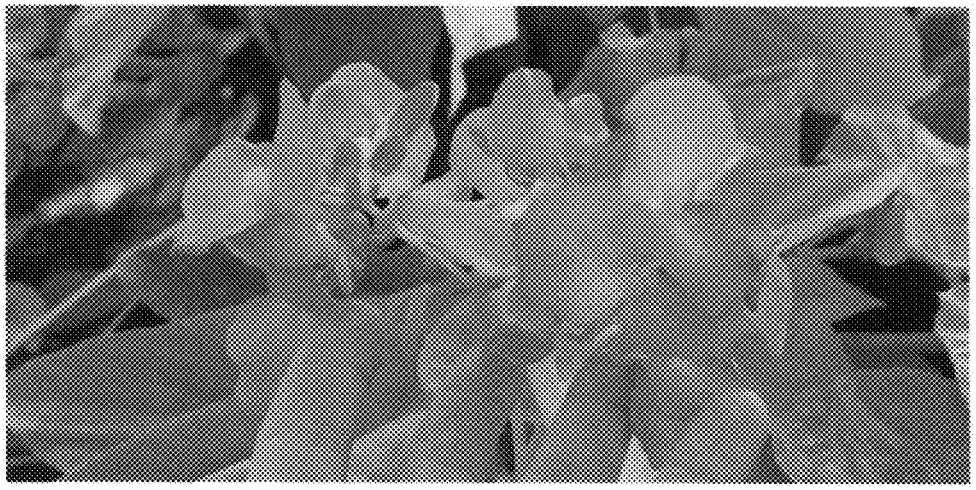

The photograph in FIG. 2 provides a close-up view of the flowers of 'Canary Wing'.

Figure 3:
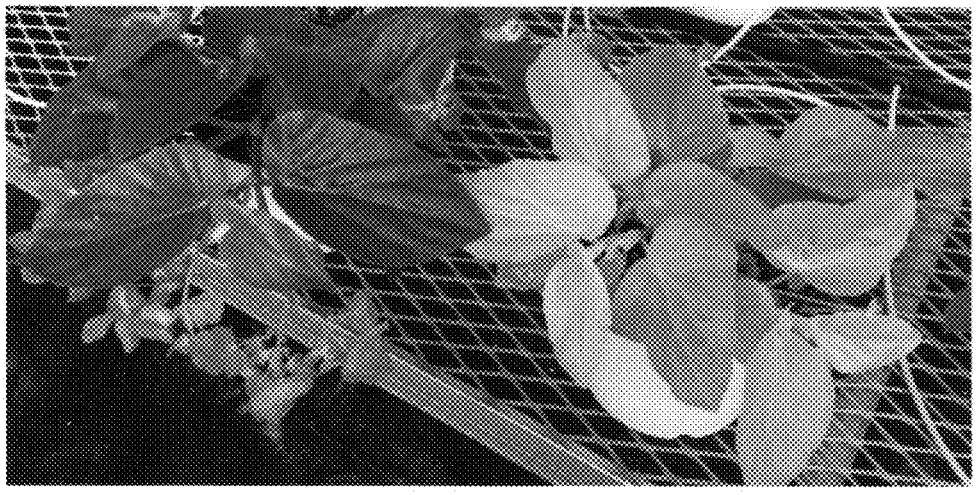

The photograph in FIG. 3 provides a comparison of the parent plant on the left and 'Canary Wing' on the right.

The colors in the photographs are as close as possible with the digital photography techniques available, the color values cited in the detailed botanical description accurately describe the colors of the new *Begonia*.

DETAILED BOTANICAL DESCRIPTION OF THE PLANT

The following is a detailed description of plants of the new cultivar 1 month in age (from a cutting) as grown in 4-inch containers in a greenhouse in Cardington, Ohio. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General plant characteristics:

*Blooming habit*.—Blooms throughout the growing season.

*Plant type*.—Annual.

*Plant habit*.—Trailing.

*Height and spread*.—Reaches an average of 30 cm in height and spread in a season in a container, one month-old plants received for data collection reached 14 cm in heght and 18 cm in width.

*Cold hardiness*.—Not applicable, grown as annual.

*Diseases and pests*.—No unique susceptibility and resistance to diseases or pests has been observed.

*Root description*.—Fleshy to fibrous.

*Growth rate*.—Vigorous.

*Propagation*.—Stem cuttings.

*Root development*.—A cutting will root and fully develop in a 4-inch container in about a month as grown in a greenhouse at 68° F.

Stem description:

*Branching habit*.—Short stems arise from base with an average of 2 side branches per branch.

*Stem size*.—An average of 5 cm in length and 7 mm in width, with side branches an average of 2 cm in length and 5 mm in width.

*Stem shape*.—Oval, irregular.

*Stem color*.—A blend of 144C and 144D and suffused with 174A on lower portion of stem.

*Stem surface*.—Satiny with sparse hairs.

*Internode length*.—Average of 9 mm.

Foliage description:

*Leaf shape*.—Ovate.

*Leaf division*.—Single.

*Leaf base*.—Cordate but asymmetric.

*Leaf apex*.—Acute.

*Leaf venation*.—Main veins are palmate from sinus, color 145C on upper and lower surface.

*Leaf margins*.—Crenate, with short bristly hairs.

*Leaf attachment*.—Petiolate.

*Leaf arrangement*.—Alternate.

*Leaf surface*.—Upper surface; glabrous and satiny, lower surface; glabrous and dull.

*Leaf color*.—Young leaves upper surface; a blend of 144B and 144C, young leaves lower surface; color between 144C and 144D, mature leaves upper surface; 144B, mature leaves lower surface; color between 144C and 144D.

*Leaf size*.—Up to 11 cm in length and 7 cm in width when mature.

*Leaf quantity*.—Average of 6 per stem 5 cm in length.

*Leaf fragrance*.—None.

*Petioles*.—An average of 1.5 cm in length and 3 mm in width, surface glabrous, about 173D in color.

Flower description:

*Inflorescence type*.—An average of 7 male flowers and 4 female flowers per flowering stem with males opening first followed by the female flowers.

*Peduncles*.—Up to 8.5 cm in length and 3 mm in width), color; a blend of 58B, 179B, 179C, and 179D in color, surface is glabrous and satiny.

*Flower lastingness*.—Male flowers about 2 days, and female flowers about 7 days, per flower, self-cleaning.

*Flower type*.—Tepals rotate on both male and female flowers with the tepals of female flowers held over showy winged ovaries.

*Flower fragrance*.—None.

*Flower number*.—Average of 12 flowers per division.

*Flower aspect*.—Nodding and outward.

*Bracts*.—Ovate in shape and clasping to node at base, rounded apex, entire margins, an average of 8 mm in length and 1 cm in width, papery texture, 177C in color.

Male flowers:

*Pedicels*.—About 1.5 cm in length and 1.5 mm in width, color; 58C in color, glabrous surface.

*Flower buds*.—Round in shape with cordate base, about 2.0 cm in length and width, a blend of 58C and 58D in color blending into 157B at basal center spot with very center of spot of 145C.

*Flower size*.—An average of 4 cm in width and 2.4 cm in length.

*Tepals*.—2 in number, rounded in shape, rounded apex, truncate base, average of 2.5 cm in width and 2.4 cm in length, glabrous on upper and lower surface, margins entire, color upper and lower surface; 58B.

*Corolla form*.—Open to an average of 45°, tepals are un-fused.

*Stamens*.—Average of 40, formed into a center cluster about 8 mm in length and 5 mm in width, stamens about 4 mm in length and 1 mm in width, filament is about 0.5 mm in width, 2 mm in length, and 13A in color, anther is about 2 mm in length, 13A in color, pollen was not observed.

Female flowers:

*Pedicels*.—About 1 cm in length and 1.5 mm in width, 58C in color, glabrous surface.

*Flower buds*.—Ovate in shape and cupped inward, an average of 2 cm in length and 1 cm in width, 157A in color and 58B on the tips of tepals.

*Flower size*.—About 3 cm in depth and 3.5 cm in diameter.

*Tepals*.—5 in number, un-fused, oblong-ovate in shape, broadly acute apex, base truncate to keel, average of 2 cm in length and 1.2 cm in width, glabrous on inner and outer surface, entire margin, color inner and outer surface; a blend of 58B, 58C, and 58D.

*Ovaries*.—Inferior, center section oblong in shape, broadly acute apex, truncate base, average of 1 cm in length and 8 mm in width, glabrous surface, color a blend of 58B, 58C, and 58D, wings; 3, triangular in shape, an average of up to 1.5 cm in width and 1.7 cm in length, 157A towards center with outer areas 58B to 58C.

*Pistils*.—3, stigmas; 2 branched, crested and curly, lobes about 3 mm in length and 2 mm in width, 13C in color, styles; stout, about 2 cm in length and 1 cm in width, 13C in color.

*Mature fruit/seed*.—Not observed.

It is claimed:

1. A new and distinct cultivar of *Begonia* plant named 'Canary Wing' as herein illustrated and described.

* * * * *